(12) United States Patent
Ishigami

(10) Patent No.: US 8,480,010 B2
(45) Date of Patent: Jul. 9, 2013

(54) SURFACE ACOUSTIC WAVE ATOMIZER

(75) Inventor: Youhei Ishigami, Yao (JP)

(73) Assignee: Panasonic Corporation, Osaka (JP)

( * ) Notice: Subject to any disclaimer, the term of this patent is extended or adjusted under 35 U.S.C. 154(b) by 148 days.

(21) Appl. No.: 13/125,136

(22) PCT Filed: Oct. 22, 2009

(86) PCT No.: PCT/JP2009/005534
§ 371 (c)(1),
(2), (4) Date: Apr. 20, 2011

(87) PCT Pub. No.: WO2010/047110
PCT Pub. Date: Apr. 29, 2010

(65) Prior Publication Data
US 2011/0192914 A1    Aug. 11, 2011

(30) Foreign Application Priority Data
Oct. 24, 2008   (JP) ................. 2008-274453

(51) Int. Cl.
*B05B 17/06*   (2006.01)
*B05B 1/08*    (2006.01)
*H01L 41/053*  (2006.01)

(52) U.S. Cl.
USPC .............. 239/102.2; 310/313 R; 310/313 B; 310/313 D

(58) Field of Classification Search
USPC ........... 239/4, 102.1, 102.2, 338; 310/313 R, 310/313 B, 313 D
See application file for complete search history.

(56) References Cited

U.S. PATENT DOCUMENTS

| 5,063,396 | A | * | 11/1991 | Shiokawa et al. ............... 347/46 |
| 5,297,734 | A | * | 3/1994 | Toda .......................... 239/102.2 |
| 5,657,926 | A | * | 8/1997 | Toda .......................... 239/102.2 |
| 5,996,903 | A | | 12/1999 | Asai et al. |
| 7,053,524 | B2 | * | 5/2006 | Edmonson et al. ....... 310/313 D |
| 7,615,909 | B2 | | 11/2009 | Kirigaya et al. |
| 2005/0126480 | A1 | | 6/2005 | Yamagata et al. |
| 2007/0202258 | A1 | * | 8/2007 | Yamagata et al. ............ 427/282 |
| 2009/0206171 | A1 | * | 8/2009 | Friend et al. ..................... 239/4 |

FOREIGN PATENT DOCUMENTS

| JP | 7-232114 | 9/1995 |
| JP | 11-207224 | 8/1999 |
| JP | 2003-071343 | 3/2003 |
| JP | 2003-136005 | 5/2003 |
| JP | 2004-190537 | 7/2004 |
| JP | 2008-104966 | 5/2008 |
| JP | 2008-104974 | 5/2008 |
| WO | 97/05960 | 2/1997 |

* cited by examiner

*Primary Examiner* — Darren W Gorman
(74) *Attorney, Agent, or Firm* — Greenblum & Bernstein, P.L.C.

(57) ABSTRACT

A surface acoustic wave atomizer includes a piezoelectric substrate which has a pattern electrode on a surface and a liquid supply member for supplying a liquid to the surface and atomizes the liquid supplied to the surface by surface acoustic wave, and between the liquid supply member and the surface of the piezoelectric substrate, a small gap is provided in an area which is designed to hold and guide the liquid and a large gap is provided in an area which is not designed to supply the liquid, so that the liquid is supplied to an atomizing area in an area away from the pattern electrode in the surface of the piezoelectric substrate by using a difference in surface tension due to sizes of the gaps. The liquid can be supplied stably by the small gap and a distribution of the liquid can be limited by the large gap.

**

A–A SECTION

B-B SECTION

C-C SECTION

SURFACE ACOUSTIC WAVE ATOMIZER

TECHNICAL FIELD

The present invention relates to an atomizer which uses surface acoustic wave.

BACKGROUND TECHNIQUE

Conventionally, there is a known phenomenon that when a liquid is supplied to a surface of a substrate such as a piezoelectric material on which surface acoustic wave is propagated, the liquid receives an energy of the surface acoustic wave, flows and vibrates, and as a result, the liquid changes to microparticles (nanoparticles) and flies. Apparatuses which atomize a liquid by using the above phenomenon are variously suggested. As a principle of atomization, for example, it is described that the surface acoustic wave (Rayleigh wave) which propagates on the surface of the substrate, after getting into the liquid, changes to surface tension wave (capillary wave) which propagates on the surface of the liquid, and as a result, mist is generated from the liquid surface.

The surface acoustic wave in the above atomizer is excited by an application of high-frequency electricity to an interdigital electrode formed on a surface of a piezoelectric substrate. The interdigital electrode, which is an electrical component, needs to be protected from a trouble such as a short circuit or rust deterioration caused by the liquid. Moreover, the liquid needs to be stably guided (fed) and supplied to a predetermined atomizing area at a constant quantity per unit time to atomize the liquid stably with high-energy efficiency. As means for liquid supply, it is considered to use a liquid surface tension or a capillary action.

Although the surface acoustic wave is not used, for example, there is a known spray head which atomizes a liquid by supplying the liquid to a surface of a discoid vibration plate which produces ultrasonic vibration of longitudinal vibration mode (refer to patent document 1, for example). In the above spray head, the liquid is supplied through an annular gap which is formed with a folded part of a cylindrical tube closely positioned to a periphery of the vibration plate, and a thickness of the liquid film is held by a surface tension of the liquid.

Moreover, there is a known atomizing apparatus provided with a piezoelectric substrate which has an interdigital electrode to excite surface acoustic wave on its surface, a spacer which is disposed around the edge of the surface of the piezoelectric substrate, and a liquid supply plate which has an outlet of mist and disposed facing the surface of the piezoelectric substrate across the spacer, and those make up a space to hold a liquid (refer to patent document 2, for example). In this atomizing apparatus, the liquid is supplied to above-mentioned space by a capillary action in a liquid leading passage communicated with the space.

PRIOR ART DOCUMENT

Patent Document

Patent document 1: Japanese Laid-Open Patent Publication No. 2003-71343

Patent document 2: Japanese Laid-Open Patent Publication No. 2008-104966

SUMMARY OF THE INVENTION

Problems to be Solved by the Invention

However, the spray head having the configuration described in the above patent document 1 does not have the interdigital electrode and so on which should be protected from contacting with the liquid, so that it does not suggest any solution for the problem such as a protection of the interdigital electrode and so on in the surface acoustic wave atomizer. Moreover, in the atomizing apparatus described in the above patent document 2, the space which holds the liquid is located at the surface in which the interdigital electrode is disposed, and the whole surface of the interdigital electrode is always adjacent to the liquid via an insulating protective film or an insulating lyophilic film. Thus, the protection of the interdigital electrode depends absolutely on the reliability of the insulating film, and therefore such a configuration is not desirable.

The present invention is to solve the above problem, and an object of the present invention is to provide a surface acoustic wave atomizer which can guide a liquid to a predetermined atomizing area on a substrate surface stably at a constant quantity per unit time and can limit a distribution of the liquid on the substrate surface, so that a stable and efficient atomization and also a deterioration control of an interdigital electrode and so on can be achieved with a simple configuration.

Means for Solving the Problems

To achieve the above problems, a surface acoustic wave atomizer according to an aspect of the present invention includes a piezoelectric substrate which has a pattern electrode on its surface to excite surface acoustic wave by applying a high-frequency voltage, and a liquid supply means for supplying a liquid to the surface of the piezoelectric substrate, wherein the atomizer atomizes the liquid supplied by the liquid supply means to the surface of the piezoelectric substrate by using the surface acoustic wave, wherein the liquid supply means has a liquid supply member which is disposed facing the surface of the piezoelectric substrate, and between the members of the liquid supply member and the surface of the piezoelectric substrate, a small gap is provided in an area where the liquid is to be held and guided and a large gap which is larger than the small gap is provided in an area where the liquid is not to be supplied, so that the liquid is supplied to an atomizing area which is in an area away from the pattern electrode on the surface of the piezoelectric substrate by using a difference in surface tension due to sizes of the gaps between the members.

In a preferred embodiment, the small gap is formed by a convexo-concave structure which is made by roughening a surface of the liquid supply member facing the surface of the piezoelectric substrate.

In a preferred embodiment, the small gap is formed in an area on the surface of the piezoelectric substrate where the surface acoustic wave is not excited.

In a preferred embodiment, the surface acoustic wave atomizer includes a support plate to support the piezoelectric substrate from its back surface, and the support plate is provided to form a clearance at a back surface of an area which separates an area where the pattern electrode is formed from an area where the gaps between the members are formed on the surface of the piezoelectric substrate.

In a preferred embodiment, the surface acoustic wave atomizer includes a contact jig which has electrode pins to apply voltage to the pattern electrode and is mounted on the piezoelectric substrate, and the contact jig has a configuration to have, in relation to the surface of the piezoelectric substrate, a large gap in a side close to the pattern electrode and a small gap which is smaller than the large gap in a side far from the pattern electrode so that the pattern electrode and the atomizing area are set away from each other.

EFFECT OF THE INVENTION

According to the present invention, the liquid can be fed to the atomizing area on the surface of the piezoelectric substrate stably at a constant quantity per unit time by a substantially constant holding force of a surface tension in the small gap, and a distribution of the liquid on the surface of the piezoelectric substrate can be limited by the large gap, so that a stable and efficient atomization and a deterioration control of the interdigital electrode and so on can be achieved.

When the small gap is formed by the convexo-concave structure made by roughening the surface of the liquid supply member facing the surface of the piezoelectric substrate, the small gap can be formed merely by roughening the surface of the liquid supply member, and the large gap is enough to be large, so that a size accuracy, which is required for a processing of the liquid supply member, is mitigated.

When the small gap is formed in the area on the surface of the piezoelectric substrate where the surface acoustic wave is not excited, the liquid can be guided to the atomizing area as calculated without a resistance from the surface acoustic wave which is pushing back the liquid.

When the support plate is provided to form the clearance at the back surface of the area which separates the area where the pattern electrode is formed from the areas where the gaps between the members are formed on the surface of the piezoelectric substrate, the clearance at the back surface cuts off the liquid guided by a capillary action, so that even if the liquid is leaked in the back surface of the piezoelectric substrate, the liquid does not flow along the back surface and does not reach the area where the pattern electrode is formed, and thus a trouble such as a short circuit or deterioration of the pattern electrode can be prevented.

When the contact jig has a configuration to have, in relation to the surface of the piezoelectric substrate, the large gap in the side close to the pattern electrode and the small gap which is smaller than the large gap in the side far from the pattern electrode so that the pattern electrode and the atomizing area are set away from each other, the liquid is prevented from approaching the pattern electrode by the large and small gaps in front of the pattern electrode, thus the trouble such as the short circuit or deterioration of the pattern electrode can be prevented.

DESCRIPTION OF THE PREFERRED EMBODIMENTS (First Embodiment)

Figure 1A:
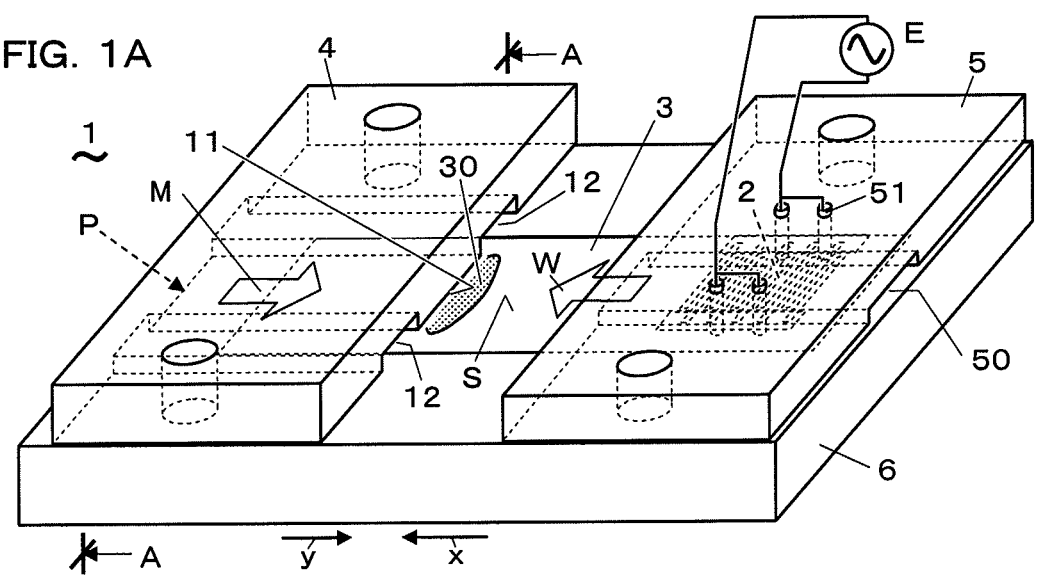
FIG. 1A is a perspective view of a surface acoustic wave atomizer according to a first embodiment of the present invention.
Figure 1B:
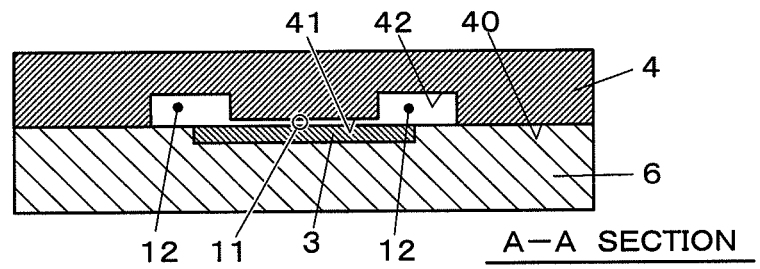
FIG. 1B is a cross-sectional view of FIG. 1A.
Figure 2:
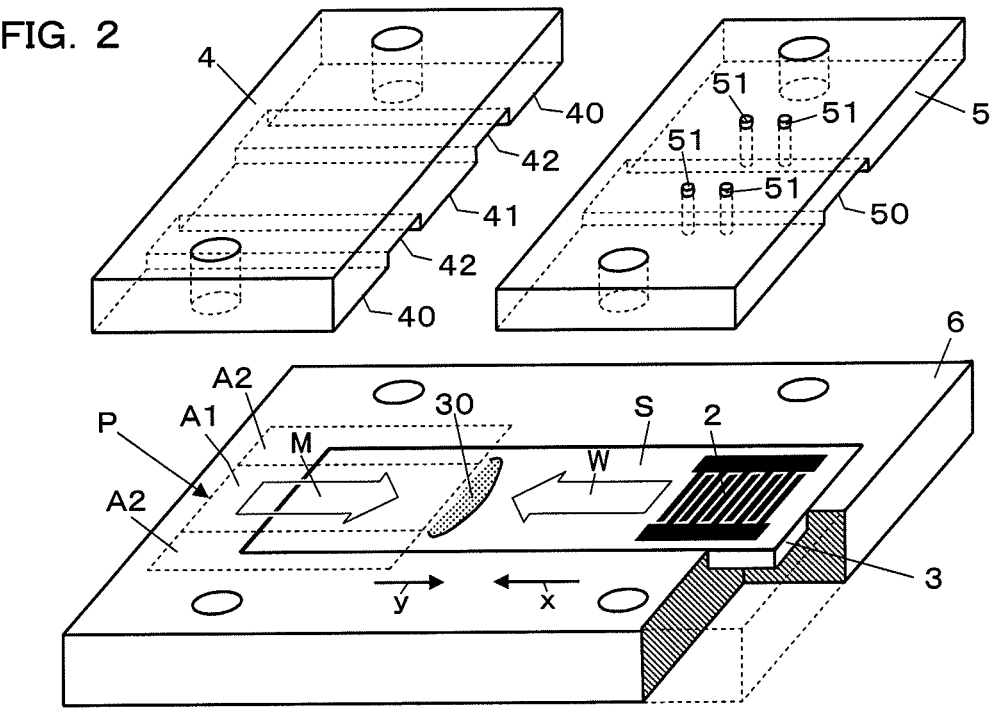
FIG. 2 is a partially broken away, exploded perspective view of the above-mentioned atomizer.

A surface acoustic wave atomizer according to embodiments of the present invention is described with reference to the drawings. FIGS. 1A, 1B, and 2 show the surface acoustic wave atomizer according to the first embodiment. A surface acoustic wave atomizer 1 includes a piezoelectric substrate 3 which has a pattern electrode 2 on a surface S to excite a surface acoustic wave W by applying a high-frequency voltage, a liquid supply member 4 for supplying a liquid M to an atomizing area 30 on the surface S of the piezoelectric substrate 3, a contact jig 5 which has electrode pins 51 to apply voltage to the pattern electrode 2 and is mounted on the piezoelectric substrate 3 from an upper side of the pattern electrode 2, and a support plate 6 which is a basis member to support the piezoelectric substrate 3 from its lower side, and atomizes the liquid M, which is supplied by the liquid supply member 4 to the surface S of the piezoelectric substrate 3, by the surface acoustic wave W which is generated on the surface S. The liquid supply member 4 makes up the liquid supply means together with a liquid container (not shown) and so on. The liquid supply member 4 forms gaps between the members which hold and guide the liquid M by a capillary action on the surface S of the piezoelectric substrate 3 and supplies the liquid M to the atomizing area 30. Details of the above configuration are described below.

The pattern electrode 2 is an electrode which is made up of two comb-like electrodes interdigitating with each other on the surface S of the piezoelectric substrate 3 (that is, interdigital transducer, IDT). Comb teeth of the pattern electrode 2 which are adjacent to each other belong to different electrodes and are arranged at a pitch of half length of a wavelength of the excited surface acoustic wave W. When applying a high-frequency (for example, MHz) voltage to the two comb-like electrodes of the pattern electrode 2 from an electrical circuit E dedicated to the high-frequency voltage applying purpose, an electrical energy is converted into a wave mechanical energy by the comb-like electrodes, and the surface acoustic wave W which is called as Rayleigh wave is excited on the surface S of the piezoelectric substrate 3. An amplitude of the excited surface acoustic wave W is fixed by an amplitude of the voltage applied to the pattern electrode 2. A length of wave packet of the excited surface acoustic wave W corresponds to a length of time the voltage is applied. The surface acoustic wave W excited by the pattern electrode 2 becomes a wave having a width corresponding to the overlap width of comb teeth in a pair of comb-like electrodes interdigitating with each other and propagated in a direction x perpendicular to the comb teeth. The above surface acoustic wave W has a feature forcing the liquid on the surface S to move in a propagation direction of the surface acoustic wave W. Moreover, because the comb-like electrodes generate the surface acoustic wave which propagates in both positive and negative directions of the direction x, a reflector may be provided so that the surface acoustic wave moving in the negative direction is reflected totally and used efficiently.

The piezoelectric substrate 3 is, for example, a substrate of a piezoelectric itself such as LiNbO$_3$ (lithium niobate). Moreover, the piezoelectric substrate 3 can also be made up of a non-piezoelectric substrate having a piezoelectric thin film such as PZT thin film (lead, zirconium, titanium alloy thin film), for example, on its surface. The surface acoustic wave W is excited on a surface of the piezoelectric thin film on the surface of the non-piezoelectric substrate. Consequently, the piezoelectric substrate 3 is enough to be a substrate having on its surface the piezoelectric part where the surface acoustic wave is excited.

Figure 3:
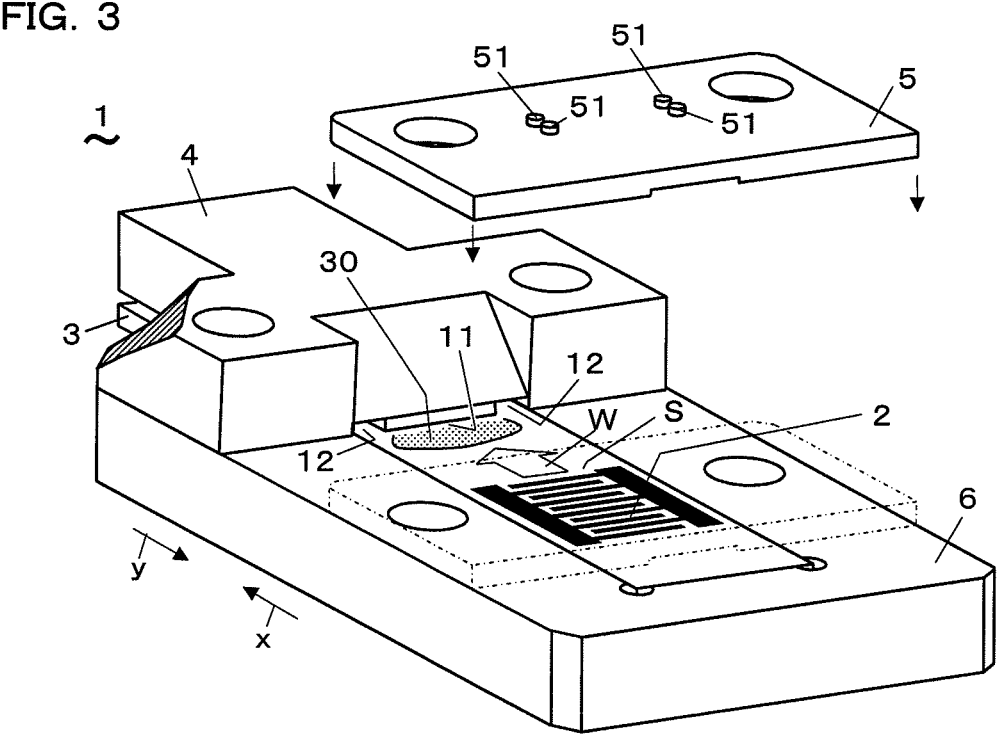
FIG. 3 is a perspective view showing a modification example of the above-mentioned atomizer.
Figure 4:
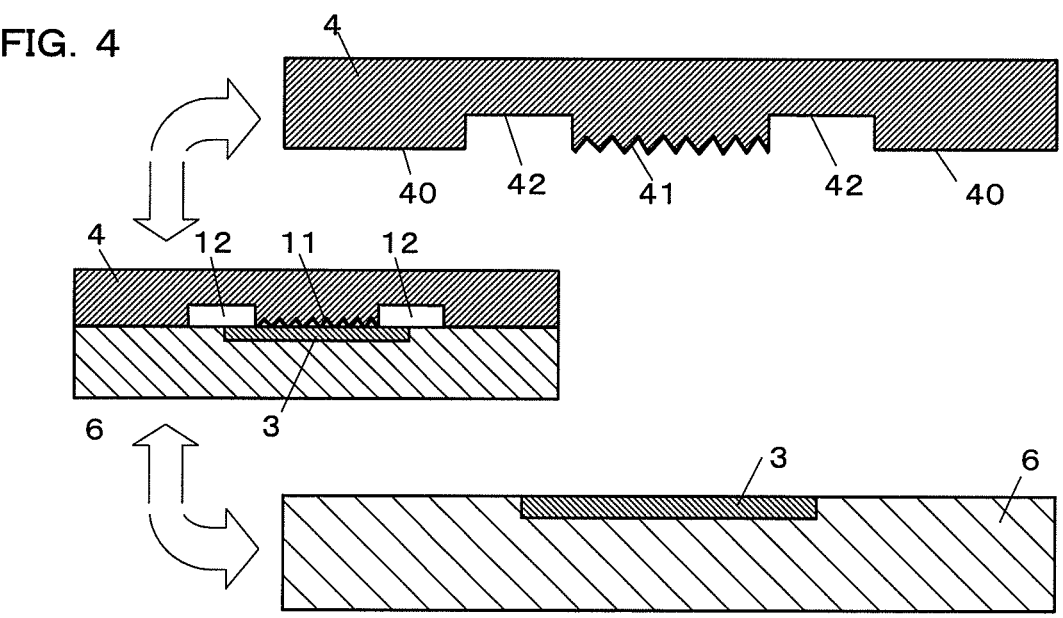
FIG. 4 is a cross-sectional exploded view of a surface acoustic wave atomizer according to a second embodiment of the present invention.
Figure 5:
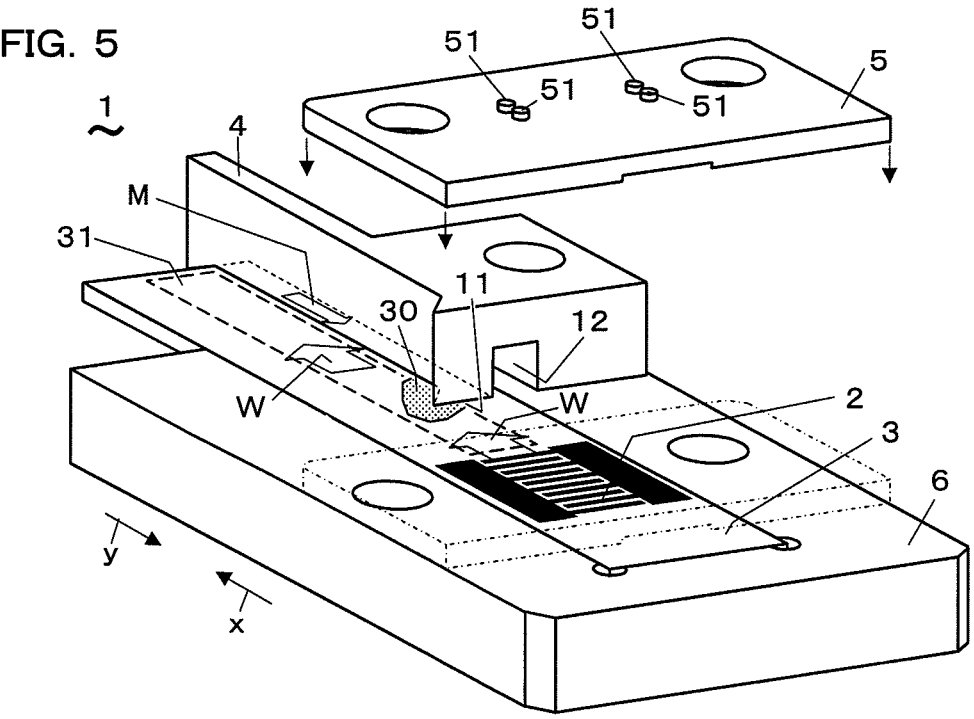
FIG. 5 is a partially exploded perspective view of a surface acoustic wave atomizer according to a third embodiment of the present invention.
Figure 6A:
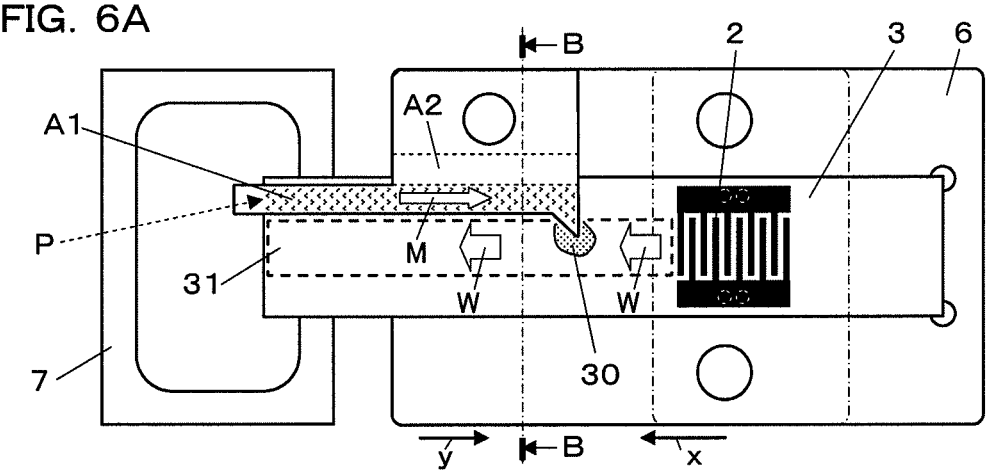
FIG. 6A is a plan view of the above-mentioned atomizer.
Figure 6B:
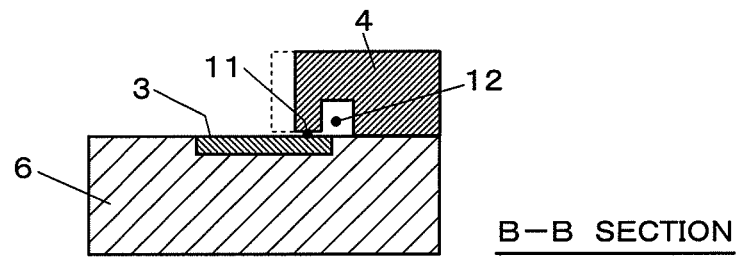
FIG. 6B is a cross-sectional view of FIG. 6A along the line B-B.
Figure 7:
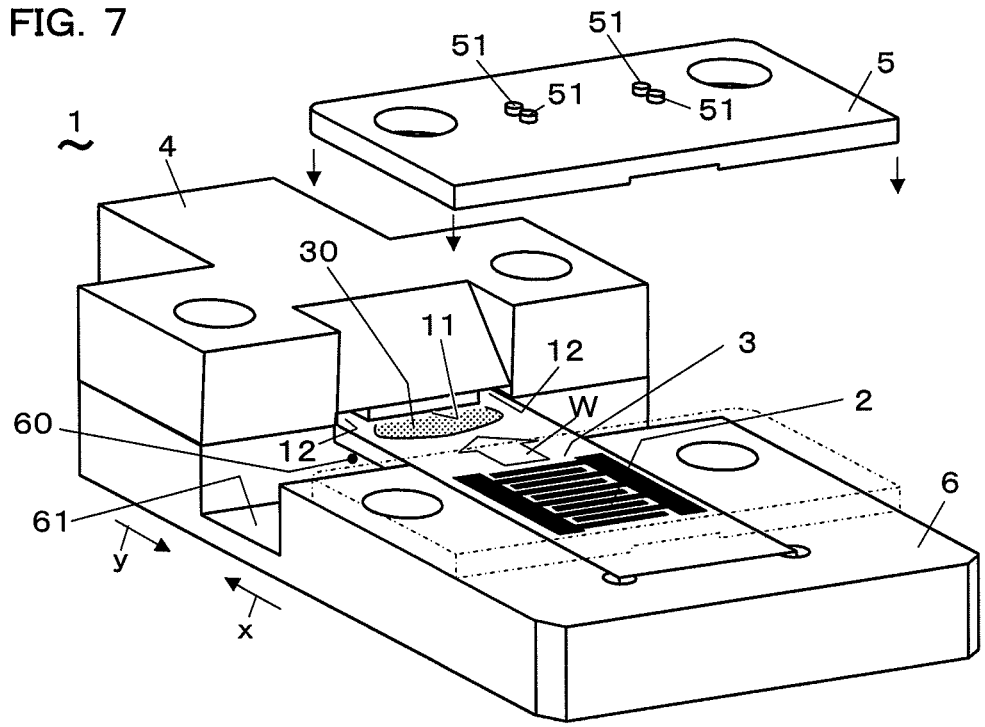
FIG. 7 is a partially exploded perspective view of a surface acoustic wave atomizer according to a fourth embodiment of the present invention.
Figure 8A:
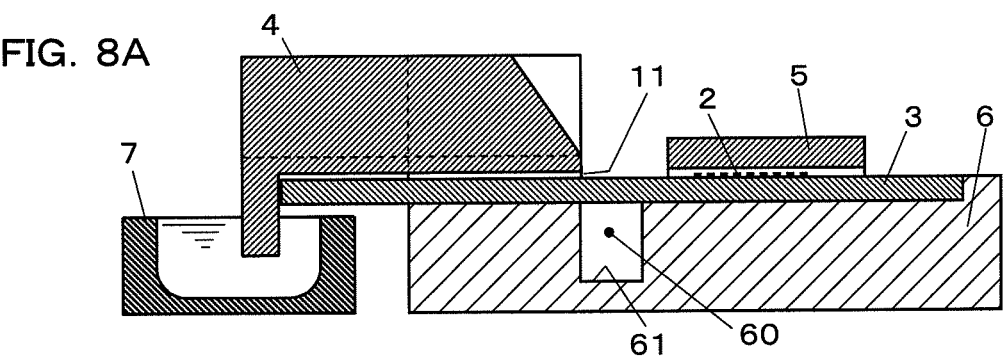
FIG. 8A is a cross-sectional view of the above-mentioned atomizer.
Figure 8B:
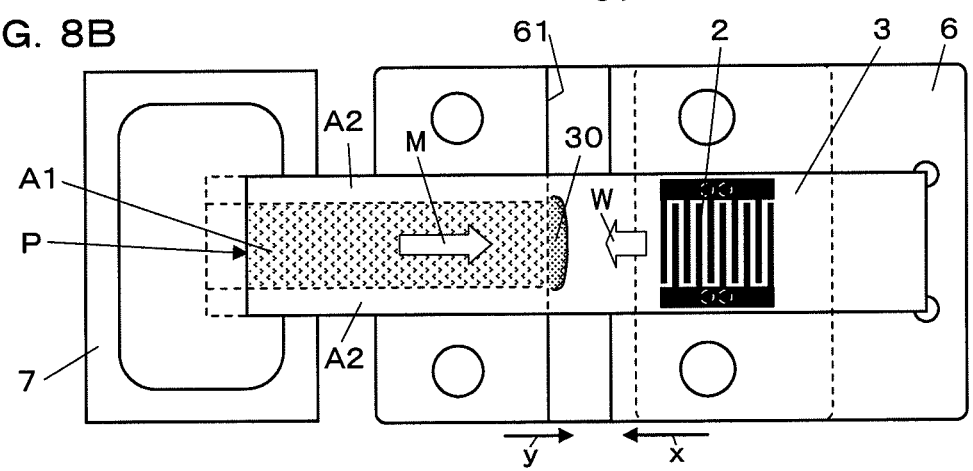
FIG. 8B is a plan view of the same.
Figure 9:
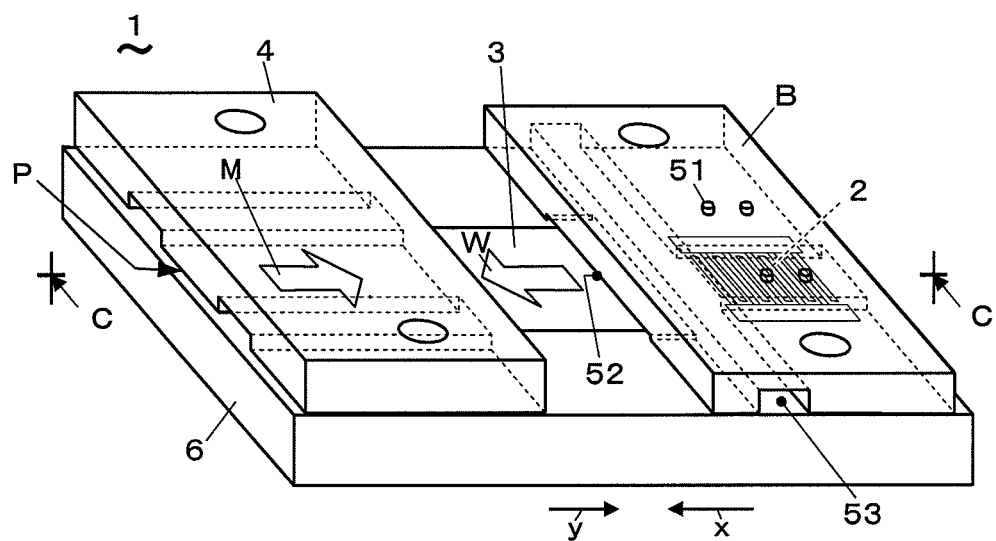
FIG. 9 is a perspective view of a surface acoustic wave atomizer according to a fifth embodiment of the present invention.
Figure 10:
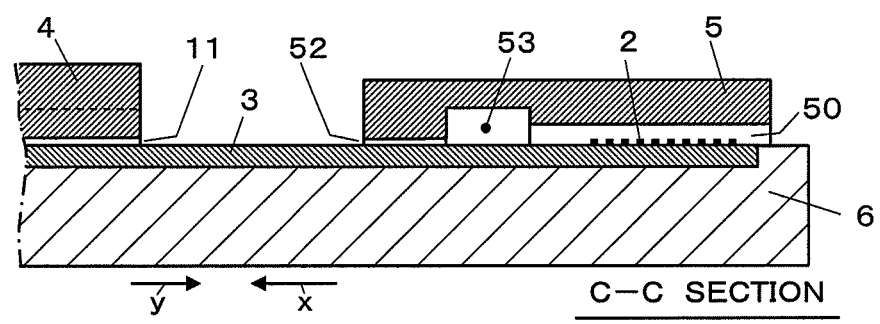
FIG. 10 is a cross-sectional view of the above-mentioned atomizer.

The piezoelectric substrate 3 in this embodiment is formed into a rectangular plate. The pattern electrode 2 is formed in one end side of the piezoelectric substrate 3 in a longitudinal direction (right side of FIGS. 1A and 2), and the liquid M is guided from other end side of the piezoelectric substrate 3 along a direction y toward a center of the piezoelectric substrate 3. The atomizing area 30 where the liquid M changes to microparticles (nanoparticles) and flies is set near the center of the piezoelectric substrate 3. That is to say, the supply position of the liquid M and atomizing area 30 on the piezoelectric substrate 30 are set in positions away from the position of the pattern electrode 2, which excites the surface acoustic wave W, toward the propagation direction of the surface acoustic wave W (direction x). Moreover, the piezoelectric substrate 3 is mounted in a recess formed in the support plate 6 so that the surfaces of piezoelectric substrate 3 and support plate 6 are flush with each other. The piezoelectric substrate 3 mounted in the recess is fixed to the support plate 6 with the contact jig 5 which is fixed to the support plate 6 with two screws (not shown). On a surface of the contact jig 5 which faces the piezoelectric substrate 3, a recess 50 is formed not to prevent the excitation and propagation of the surface acoustic wave W.

The liquid supply member 4, which is a substantially rectangular parallelepiped member, is disposed facing the surface S of the piezoelectric substrate 3 from an upper side of the piezoelectric substrate 3 and is fixed to the support plate 6 with two screws (not shown). Two grooves 42 are formed on a lower surface 40 (a surface facing the piezoelectric substrate 3) of the liquid supply member 4 along the longitudinal direction of the piezoelectric substrate 3 (direction y), and a surface 41 located between the grooves 42 is formed as a backed surface away from the lower surface 40. By disposing the liquid supply member 4 having such a configuration on the support plate 6, a small gap 11 is formed between the surface 41 and the surface S of the piezoelectric substrate 3 and a large gap 12 is formed between the grooves 42 and the surface S of the piezoelectric substrate 3. An area A1 in which the small gap 11 is formed on the surface S of the piezoelectric substrate 3 (FIG. 2) is an area to hold and guide the liquid M, and each area A2 in which the large gap 12 is formed is an area to prevent the liquid M from being guided. The small gap 11 is a gap of approximately 0.1 to 0.3 μm, for example. The large gap 12 is a gap of approximately 300 to 500 μm, for example.

The liquid M is supplied from an end P of the area A1 which is located in a side opposite to the direction y. The supply of the liquid M to the end P can be done, for example, by dropping the liquid M or by using an action caused by a small gap formed by employing another member, a porous material, a fibrous material, and so on.

The above liquid supply member 4, in other words, is a member which supplies the liquid M to the atomizing area 30 at the area away from the pattern electrode 2 on the surface S of the piezoelectric substrate 3 by forming the small gap 11 in an area designed to hold and guide the liquid M and the large gap 12 in an area designed not to supply the liquid M and by using a difference in surface tension of the liquid M due to sizes of the gaps between the members. The liquid M comes out to an end of the area A1 in the direction y, and an area located in a forward direction of the direction y is the atomizing area 30. The liquid M keeps its shape by the surface tension and exposes its liquid surface around the forward area of the area A1, however, the liquid M is consumed by the atomization in the atomizing area 30 side, so that the liquid M is supplied continuously.

According to the surface acoustic wave atomizer 1 of this embodiment, the liquid can be fed to the atomizing area 30 on the piezoelectric substrate surface S stably at a constant quantity per unit time by a substantially constant holding force of the surface tension in the small gap 11, and a distribution of the liquid M on the piezoelectric substrate surface S can be limited by the large gap 12, so that a stable and efficient atomization and deterioration suppression of the interdigital transducer and so on can be achieved. When the liquid M is not atomized and remains in a liquid drop state, on the piezoelectric substrate surface S, in case of low-power atomization, setting a case of high-power atomization aside, the energy of the surface acoustic wave W is absorbed by the liquid drop, and thereby the atomization stops or becomes unstable. The surface acoustic wave atomizer 1 of this embodiment can prevent the occurrence of the liquid drop by the effect of the small gap 11, so that the atomization can be performed stably even by the low-power electricity. The holding and guiding of the liquid M by the small gap 11 has a common feature with a concept of a waveguide by a microstrip line in a high-frequency electrical circuit. That is to say, the liquid M can be guided to a desired position without any leakage from a line path by forming the line path made of the small gap 11 (the line path by the area A1) in a desired shape on the surface S of the piezoelectric substrate 3.

FIG. 3 shows a modification example of the surface acoustic wave atomizer 1 of this embodiment. In this modification example, the piezoelectric substrate 3 is set in a state that one side of its where the pattern electrode 2 is provided is mounted and fixed in the recess in the support plate 6, and another end of its where the small gap 11 is formed protrudes from the support plate 6 in a cantilever manner. Accordingly, an area where the small gap 11 is formed (not shown, refer to the area A1 in FIG. 8B described hereinafter) does not have a joint line between the members (a slit between the members). Here, the joint line between the members means, for example in FIG. 2, a line which is formed by an outcrop of a contacting portion of two surfaces, one is an end surface of the piezoelectric substrate 3 located in the area A1 side and the other is a wall surface of an opening in the recess in the support plate 6. In the structure of FIG. 2, the area A1 passes across the joint line, so that the liquid M leaks in the slit between the members at this joint line. In contrast, in the surface acoustic wave atomizer 1 of this modification example, there is no joint line in the area where the liquid M is guided, so that the liquid is suppressed from reaching the back surface of the piezoelectric substrate 3.

The suppression of the liquid M reaching (leaking in) the slit between the members is done also by the large gap 12 shown in FIGS. 1A and 3, for example. Here, a general relation of the leakage of liquid into a slit between members is described. Generally, there is a slit between members, and when the liquid has contact with the slit, the leakage of the liquid into the slit occurs notably. There is a method to prevent the leakage of the liquid structurally in such a way as to "make the gap of slit to zero" or "reduce the surface tension generated on the liquid". However, it is difficult to zero the gap from a standpoint of dimension accuracy and structure. Thus, in the embodiment, the large gap 12 generated by the groove 42 is provided between the area A1 where the liquid M is guided and a part where the leakage of the liquid M is to be avoided, so that a part where the surface tension is low is placed, and thus the liquid does not leak into the joint line between the members (the slit between the members). Moreover, in the modification example of FIG. 3, an inclined surface is formed in an end surface of the liquid supply member 4 at the atomizing area 30 side. The inclined surface is provided not to prevent flight of the atomized liquid particles.

The surface acoustic wave atomizer 1 is used, for example, as a medical mist aspirator which is driven by a low-power dry battery. In this case, the liquid M to be atomized is water or a medical solution which is made by dissolving chemicals in water. Moreover, when driven by a relatively high-power electricity, the surface acoustic wave atomizer 1 is used as an anti-drying humidity regulation apparatus, for example.

(Second Embodiment)

A surface acoustic wave atomizer according to the second embodiment is described with reference to FIG. 4. A surface acoustic wave atomizer 1 of this embodiment differs from that of the first embodiment in a method of forming a small gap 11 and is similar in the other point. That is to say, a surface 41 located between two grooves 42 in a lower surface 40 of the liquid supply member 4 is, instead of formed as a backed surface away from the lower surface 40, formed to have a convexo-concave structure which is made by roughening the lower surface 40. The above surface 41 on which the convexo-concave structure is made by roughening the lower surface 40, by having contact with a surface S of the piezoelectric substrate 3, has an effect equal to the small gap 11 of the first embodiment.

The above small gap 11 in the first embodiment is approximately 0.1 to 0.3 μm and thereby is very small, so that it is often affected by a work accuracy and mounting error. It is well known that when two members are fixed to each other with a screw, a liquid gets into a joint gap between the members caused by roughness of facing surfaces of the members. The liquid supply member 4 of this embodiment is made up based on such background.

According to the surface acoustic wave atomizer 1 of this embodiment, the small gap 11 can be formed merely by roughening the surface of the liquid supply member 4, and the large gap only needs to be large enough, so that a size accuracy required for a processing of the liquid supply member 4 is mitigated. That is to say, it is not necessary to perform a precise work to form the small gap 11 for guiding a liquid M, nevertheless, the liquid M can be guided to an area which is designed to guide the liquid M by using the surface roughness. In this case, the grooves 42 are formed, to prevent the liquid M from being guided, in both sides of a line path for guiding the liquid M. Moreover, the convexo-concave structure by the roughness can be formed not only in the surface 41 but also in an entire surface of the lower surface 40, and the line path for guiding the liquid M can be defined by the grooves 42.

(Third Embodiment)

FIGS. 5 and 6 show a surface acoustic wave atomizer according to the third embodiment. A surface acoustic wave atomizer 1 of this embodiment differs from those of the first and second embodiments in a position of forming the small gap 11 and is similar in the other point. That is to say, the small gap 11 is formed in an area on a surface of a piezoelectric substrate 3 where the surface acoustic wave W is not excited. An area 31 located along a center line in the longitudinal direction of the piezoelectric substrate 3 is an area through which the surface acoustic wave W propagates, and there is no surface acoustic wave W in areas on both sides of the area 31. An area A1 which holds and guides the liquid M is formed in an area on one of the both sides of the area 31 in which there is no surface acoustic wave W. Moreover, at the end portion of the liquid supply member 4 which is located in the atomizing area 30 side, a projection which is directed to the center line of the piezoelectric substrate 3 is formed, and the small gap 11 is continuously formed also on a lower surface of the projection. That is to say, the small gap 11 is formed only around the atomizing area 30 in the area through which the surface acoustic wave W is propagated. A liquid container 7 is shown in FIG. 6A. The liquid M is supplied from the liquid container 7 to the area A1 by a member which hangs down from an end P of the liquid supply member 4.

According to the surface acoustic wave atomizer 1 of this embodiment, the liquid M can be guided to the atomizing area 30 as calculated with no resistance from the surface acoustic wave W which pushes back the liquid M. As described above, the surface acoustic wave W forces the liquid on the surface to move in the propagation direction of the surface acoustic wave W, however, according to the small gap 11 of this embodiment, the liquid M can be guided to the atomizing area 30 efficiently, and also the atomizing area 30 can be localized. On the contrary, the atomizing area 30 can be distributed in plural areas by providing plural projections which are directed to the center line of the piezoelectric substrate 3 from the liquid supply member 4 along the longitudinal direction of the piezoelectric substrate 3. Moreover, in this embodiment, one example is described that the liquid supply member 4 is placed in the one side of the piezoelectric substrate 3, however, the liquid supply member 4 may also be disposed in both sides of the piezoelectric substrate 3.

(Fourth Embodiment)

FIGS. 7 and 8 show a surface acoustic wave atomizer according to the fourth embodiment. A surface acoustic wave atomizer 1 of this embodiment differs from those of the first to third embodiments in a structure of the support plate 6 and is similar in the other point. That is to say, the support plate 6 of this embodiment is provided to form a clearance 60 at a back surface of an area which separates an area where the pattern electrode 2 is formed from the areas A1 and A2 where the gaps between the members are formed on the surface of the piezoelectric substrate 3. The clearance 60 is formed by a groove 61 which is made in the support plate 6.

According to the surface acoustic wave atomizer 1 of this embodiment, the clearance 60 on the back surface of the piezoelectric substrate 3 cuts off the liquid guided by a capillary action, so that even if the liquid gets into the back surface of the piezoelectric substrate 3, the liquid M does not flow along the back surface and does not reach any more the area where the pattern electrode 2 is formed, and thus a trouble such as a short circuit or deterioration of the pattern electrode 2 can be prevented.

(Fifth Embodiment)

FIGS. 9 and 10 show a surface acoustic wave atomizer according to the fifth embodiment. A surface acoustic wave atomizer 1 of this embodiment differs from those of the first to fourth embodiments in a structure of a contact jig 5 and is similar in the other point. That is to say, the contact jig 5 of this embodiment has a configuration to have, in relation to the surface of the piezoelectric substrate 3, a large gap 53 in a side close to a pattern electrode 2 and a small gap 52 in a side far from the pattern electrode 2 so that the pattern electrode 2 and the atomizing area 30 are set away from each other by the gaps 52 and 53.

According to the surface acoustic wave atomizer 1 of this embodiment, the liquid is prevented from approaching the pattern electrode 2 by the large and small gaps 52 and 53 in the atomizing area 30 side of the pattern electrode 2, thus the trouble such as the short circuit or deterioration of the pattern electrode 2 can be prevented.

Although the respective embodiments are described, the present invention is not limited to the above configurations, and various modification are applicable. For example, a configuration which combines the configurations of the above embodiments is also applicable.

DESCRIPTION OF THE NUMERALS

1 surface acoustic wave atomizer
2 pattern electrode
3 piezoelectric substrate
4 liquid supply member
5 contact jig
6 support plate
11 small gap
12 large gap
30 atomizing area
51 electrode pin
60 clearance
S surface
M liquid
W surface acoustic wave

What is claimed is:

1. A surface acoustic wave atomizer, comprising:
a piezoelectric substrate which has a pattern electrode on its surface to excite surface acoustic wave by applying a high-frequency voltage; and
a liquid supplier for supplying a liquid to the surface of the piezoelectric substrate, wherein the atomizer atomizes the liquid supplied by the liquid supplier to the surface of the piezoelectric substrate by using the surface acoustic wave, wherein
the liquid supplier has a liquid supply member which is disposed facing the surface of the piezoelectric substrate from an upper side of the piezoelectric substrate, and between the liquid supply member and the piezoelectric substrate, a small gap is provided in an area where the liquid is to be held and guided and a large gap which is larger than the small gap is provided in an area where the liquid is not to be supplied, so that the liquid is supplied to an atomizing area which is in an area away from the pattern electrode on the surface of the piezoelectric substrate by using a difference in surface tension due to sizes of the gaps.

2. The surface acoustic wave atomizer according to claim 1, wherein the small gap is formed by a convexo-concave structure which is made by roughening a surface of the liquid supply member facing the surface of the piezoelectric substrate.

3. The surface acoustic wave atomizer according to claim 1, wherein the small gap is formed in an area on the surface of the piezoelectric substrate where the surface acoustic wave is not excited.

4. The surface acoustic wave atomizer according to claim 1, comprising:
a support plate to support the piezoelectric substrate from its back surface, wherein
the support plate is provided to form a clearance between an area where the pattern electrode is formed and an area where the gaps between the liquid supply member and the piezoelectric substrate are formed on the surface of the piezoelectric substrate.

5. The surface acoustic wave atomizer according to claim 1, comprising:
a contact jig which has electrode pins to apply voltage to the pattern electrode and is mounted on the piezoelectric substrate, wherein
the contact jig has a configuration to have, in relation to the surface of the piezoelectric substrate, a large gap in a side close to the pattern electrode and a small gap which is smaller than the large gap in a side far from the pattern electrode so that the pattern electrode and the atomizing area are set away from each other.

\* \* \* \* \*